United States Patent [19]
Nielsen et al.

[11] 4,262,148
[45] Apr. 14, 1981

[54] SYNTHESIS OF HEXANITROBENZENE

[75] Inventors: Arnold T. Nielsen, China Lake; Ronald L. Atkins; William P. Norris, both of Ridgecrest, all of Calif.

[73] Assignee: The United States of America as represented by the Secretary of the Navy, Washington, D.C.

[21] Appl. No.: 113,865

[22] Filed: Jan. 18, 1980

[51] Int. Cl.³ ............................................. C07C 79/10
[52] U.S. Cl. ................................................... 568/932
[58] Field of Search ................................ 568/932, 934

[56] References Cited
PUBLICATIONS

Nielsen et al., J. Org. Chem., Mar. 30, 1979, pp. 1181 to 1182.
Orlova, Chemistry and Technology of High Explosive Substances, Publication, "Khimia," Leningrad, 1973, p. 140.

Primary Examiner—Leland A. Sebastian
Attorney, Agent, or Firm—R. S. Sciascia; W. Thom Skeer; Lloyd E. K. Pohl

[57] ABSTRACT

Hexanitrobenzene is prepared by oxidizing the amine group of pentanitroaniline with $H_2O_2$ in $H_2SO_4$. The compound is a high density explosive.

6 Claims, No Drawings

SYNTHESIS OF HEXANITROBENZENE

BACKGROUND OF THE INVENTION

1. Field of the Invention

This invention relates to methods for preparing aryl compounds having a multiplicity of nitro groups attached. More specifically, this invention relates to a method for the preparation of hexanitrobenzene.

2. Description of the Prior Art

Hexanitrobenzene is of great interest to those concerned with explosives. Aryl compounds with large numbers of nitro groups on the rings are well known to be explosives. A typical example is trinitrotoluene which is more commonly known simply as TNT. Orlova reports a method for preparing hexanitrobenzene in "Chemistry and Technology of High Energy Explosive Substances," Khimia (1973). However, the authors of this specification were unable to duplicate the results of the Russian author. Accordingly, the authors of this specification, after a considerable amount of experimentation, developed the hereinafter disclosed method for the preparation of hexanitrobenzene.

SUMMARY OF THE INVENTION

According to this invention, hexanitrobenzene is prepared by reacting pentanitroaniline with $H_2O_2$ in $H_2SO_4$ at a temperature in the range from 25° to 30° C.

DESCRIPTION OF THE PREFERRED EMBODIMENT

Hexanitrobenzene may be prepared by carrying out the procedure set forth in the following specific example.

EXAMPLE

Pentanitroaniline (1.0 g) is dissolved in 50 mL of fuming $H_2SO_4$ (20% $SO_3$). After cooling to 5° C., 5 mL of 98% $H_2O_2$ is slowly added, keeping the temperature below 30° C. The solution, protected by a drying tube, is stirred at 25°–30° C. for 24 hours and at 0° C. for 1 hour. The precipitated product is removed by filtration through a sintered glass funnel and washed with concentrated $H_2SO_4$ (additional product is obtained by extraction of the filtrate with methylene chloride; the extracts should be worked up immediately and not stored). It is dissolved in pure, dry, warm chloroform and the solution is decanted through a short column of anhydrous $MgSO_4$. The filtrate after concentration at 25° C. to a volume of 10 mL and chilling at 0° C. for several hours, deposits small, chunky, pale yellow prisms of hexanitrobenzene: 0.63 g (58%); mp 240°–265° C. dec; concentration of the filtrate gives 0.14 g of additional product, mp 195°–245° C. The first crop on sublimation gives very pale yellow prisms: mp 246°–262° C. (lit: mp 240°–258° C.) (moisture must be excluded during the isolation operations); $^{13}C$ NMR $(CD_2Cl_2)\delta$ 138.7 relative to tetramethylsilane=O (lit. 139.0 ); IR (KBr) 1560, 1320, 887 cm$^1$; mass spectrum, strong m/e at 348 with very little fragmentation.

Anal. Calcd for $C_6N_6O_{12}$: C, 20.70; N, 24.14. Found: C, 20.67; H, 0.00; N, 23.74.

In carrying out the foregoing procedure, 100% $H_2SO_4$ may be used in lieu of the fuming $H_2SO_4$ specified. Also the times of reaction (24 hours at 25°–30° C.) is not critical. The reaction time may be varied from as little as 5 to 6 hours up to an infinite amount of time. The 1 hour reaction time at 0° C. is not necessary. The hexanitrobenzene precipitates out during the reaction carried on at 25°–30° C.

Hexanitrobenzene may be utilized as an explosive in the same manner that other solid, crystalline explosive materials are utilized.

What is claimed is:

1. A method for preparing hexanitrobenzene comprising the steps of:
   A. dissolving pentanitroaniline in $H_2SO_4$ to form a solution;
   B. adding $H_2O_2$ to the solution while the solution is held at a temperature below 30° C. to form a reaction mixture; and
   C. allowing the pentanitroaniline and $H_2O_2$ to react at a temperature in the range of from 25° to 30° C.

2. A method according to claim 1 wherein the reaction of step C is carried out for about 24 hours.

3. A method according to claim 2 wherein the 24 hour reaction is followed by cooling the reaction mixture to 0° C. and holding it at that temperature for about 1 hour.

4. A method according to claim 1 wherein the $H_2SO_4$ is fuming $H_2SO_4$ containing 20% oleum.

5. A method according to claim 4 wherein the reaction of step C is carried out for about 24 hours.

6. A method according to claim 5 wherein the 24 hour reaction is followed by cooling the reaction mixture to 0° C. and holding it at that temperature for about 1 hour.

* * * * *